United States Patent [19]

Schwabe

[11] Patent Number: 5,399,348
[45] Date of Patent: Mar. 21, 1995

[54] **EXTRACT FROM *GINKGO BILOBA* LEAVES, ITS METHOD OF PREPARATION AND PHARMACEUTICALS CONTAINING THE EXTRACT**

[75] Inventor: Klaus-Peter Schwabe, Karlsruhe, Germany

[73] Assignee: Dr. Willmar Schwabe GmbH & Co., Karlsruhe, Germany

[21] Appl. No.: 905,167

[22] Filed: Jun. 24, 1992

Related U.S. Application Data

[63] Continuation of Ser. No. 625,729, Dec. 4, 1990, abandoned.

[30] Foreign Application Priority Data

Dec. 4, 1989 [DE] Germany ............ 39 40 091.3

[51] Int. Cl.$^6$ ............ A61K 35/78; A61K 31/70
[52] U.S. Cl. ............ 424/195.1; 514/27
[58] Field of Search ............ 424/195.1; 514/27

[56] References Cited

U.S. PATENT DOCUMENTS

| | | | |
|---|---|---|---|
| 4,708,949 | 11/1987 | Liu | 514/26 |
| 4,753,929 | 6/1988 | Matsumoto | 514/27 |
| 4,886,904 | 12/1989 | Tanaka | 560/249 |
| 4,981,688 | 1/1991 | Ayroles | 424/195.1 |

FOREIGN PATENT DOCUMENTS 0324197 7/1989 European Pat. Off. .

OTHER PUBLICATIONS

Nakanishi, K., et al., *The Gingkolides* pp. 89–113 (1967).
Maruyama, M., et. al. "The Ginkgolides I. Isolation and Characterization of the Various Groups" Tetra. Lett. No. 4, pp. 299–302 (1967).
Okabe, K., et. al. "Gingkolides" J. Chem. Soc. pp. 2201–2206 (1967).
Nakanishi, K., et. al. J. Am. Chem. Soc. 93: 3544–3547 (1971).
Gellerman, J. L. et. al. Analyse biologischer Materialien Ab. No. 1619 (1968).
Gellerman, J. L. *Phytochem.* 15: 1959–1961 (1976).
Hill, G. A. et. al. *J. Am. Chem. Soc.* 56: 2736–2738 (1934).
Sowers, W. F. et. al., *Arch. Derm.* 91: 452–456 (1965).
Nakamura, T. *Contact Derm.* 12: 281–282 (No. 5, 1985).
Becker, L. E. et. al. *J. Am. Med. Assoc.* 231: 1162–1163 (No. 11, 1975).
Chemical Abstracts vol. 101 No. 7 Aug. 13, 1984 #60122e Kuraray.
Kirk-Othmer Concise Encyclopedia of Chem Technology John Wiley & Sons, N.Y. 1985 p. 1235.
The Merck Index 11th Ed 1989 Merck & Co Rahway N.J. #4320.

*Primary Examiner*—Michael G. Wityshyn
*Assistant Examiner*—Ralph Gitomer
*Attorney, Agent, or Firm*—Kenyon & Kenyon

[57] ABSTRACT

The invention relates to an improved extract from Ginkgo biloba leaves, a method of preparation of the same and pharmaceuticals containing the extract.

16 Claims, No Drawings

EXTRACT FROM *GINKGO BILOBA* LEAVES, ITS METHOD OF PREPARATION AND PHARMACEUTICALS CONTAINING THE EXTRACT

This application is a continuation of application Ser. No. 07/625,729, filed on Dec. 4, 1990, now abandoned.

The invention relates to an improved extract from Ginkgo biloba leaves, a method of preparation of the extract and the pharmaceuticals containing the extract.

Extracts from the leaves of Ginkgo biloba have been used for a long time for the therapy of peripheral and cerebral arterial circulatory disturbances. Methods of preparation of Ginkgo biloba extracts with a greatly enriched content of flavone glycosides as the active components are known; see DE-B 17 67 098 and DE-B 21 17 429. These extracts are also referred to as Ginkgo biloba monoextracts.

EP-A 0 324 197 describes a method of preparation of an extract from Ginkgo biloba leaves in which an aqueous solution of a lower alcohol or ketone, obtained after extraction of the leaves, is concentrated in the presence of kieselguhr. The resultant aqueous suspension is filtered through kieselguhr, the fitrate is extracted with butanone and the extract is freed from the solvent.

EP-A 330 567 relates to a method of preparation of an extract from Ginkgo biloba leaves in which the crushed leaves are extracted with an aqueous ketone compound. This extract is concentrated until biflavones and hydrophobic compounds precipitate. After filtration the aqueous concentrate is rendered alkaline, whereby the proanthocyanidins precipitate.

After separation of the precipitate and acidification of the filtrate, a liquid-liquid-extraction is carried out with a $C_{4-6}$-ketone compound in the presence of ammonium sulfate. The extract is obtained after stripping of the ketone compound.

DE-A 35 14 054 has disclosed that the ginkgolides, known components of the Ginkgo biloba leaves which are terpenoid substances with lactone structure (see K. Nakanishi, Pure and Applied Chemistry, Vol. 14 (1967), 89–113, and M. Maruyama et al., Tetrahedron Letters (1967), 299–302 and 303–319, and K. Okabe et al., J. Chem. Soc. (1967), 2201–2206), can be used to treat illnesses and similar conditions caused by PAF ("Platelet Activating Factor").

The use of bilobalide, a further substance contained in the Ginkgo biloba leaves, is known from DE-A 33 38 995 and the corresponding U.S. Pat. No. 4,571,407 for the treatment of demyelinating neuropathies, encephalopathies and cerebral edemas. Bilobalide is a sesquiterpene lactone structurally related to ginkgolides (see K. Nakanishi et al., R. T. Major et al., and K. Weinges et al., J. Am. Chem. Soc., Vol. 93 (1971), 3544–3546).

Besides the compounds mentioned above, Ginkgo biloba leaves also contain so-called ginkgolic acids (anacardic acids). These compounds are 6-alkylsalicylic acids with n-$C_{13}$- to n-$C_{19}$-alkyl groups with 0 to 3 double bonds; see J. L. Gellermann et al., Phytochemistry, Vol. 15 (1976), 1959–1961 and Analytic. Chem., Vol. 40 (1968), 739–743.

"Ginkgol", a phenol substituted with the corresponding alkyl group, can be obtained either biogenetically by decarboxylation of the ginkgolic acids or during the technical processing of the Ginkgo biloba leaves; see Kawamura, Japan, J. Chem., Vol. 3 (1928), 91–93.

The ginkgolic acids and ginkgols in Ginkgo biloba are accompanied by corresponding derivatives with a further phenolic hydroxyl group in 4-position, the 6-alkylresorcylic acids or 5-alkylresorcins; see J. Gellermann et al., Phytochemistry, Vol. 15 (1976), 1959–1961. These resorcin derivatives are responsible for the toxic effects and especially for the strong allergies and contact dermatitis caused by toxicodendron plants; see G. A. Hill et al., J. Am. Chem. Soc., Vol. 56 (1934), 2736–2738.

Cases of strong allergic reactions after contact with Ginkgo fruits are known; see W. F. Sowers et al., Arch. Dermatol., Vol. 91 (1965), 452–456, and T. Nakamura, Contact Dermatitis, Vol. 12 (1985), 281–282. Serious mucosal disturbances after eating Ginkgo fruits have been described; see L. E. Becker and G. B. Skipworth, J. Am. Med. Assoc., Vol. 231 (1975), 1162–1163. Allergic skin reactions also occur occasionally on collecting or handling Ginkgo leaves.

The significance of allergies caused by alkylphenol compounds from anacardiaceae and ginkgoaceae is evident from the development of substances and methods of desensitisation described in patent literature (see U.S. Pat. No. 4,428,965) against the allergies caused by alkylphenol compounds.

Commercial extracts from Ginkgo biloba leaves contain between 50 and 10,000 ppm ginkgolic acids.

The extracts from Ginkgo biloba leaves prepared by the known methods in DE-B 17 67 098 and DE-B 21 17 429 are substantially free of alkylphenol compounds because the lipophilic components of the extract are removed by a liquid-liquid-extraction of the aqueous acetone extract with a substantially water-immiscible lipophilic solvent, e.g. with a chlorinated aliphatic lower hydrocarbon such as carbon tetrachloride. However, in this step, the therapeutically valuable ginkgolides and the bilobalide are also considerably reduced so that their content in the final product in Example 1 of DE-B 21 17 429 is a maximum of 0.5% in the case of ginkgolides A, B, C and J in total and approximately 0.3% in the case of bilobalide. The quantity of flavone glycosides, however, is greatly increased during this step, namely from 3 to 4% in the crude extract to approximately 24% in the final product.

The object of the present invention therefore is to provide an extract from Ginkgo biloba leaves which is substantially free of alkylphenol compounds, has a high content of flavone glycosides and which contains substantially all of the ginkgolides and bilobalide present in the leaves used.

A further object of the invention is to provide a method of preparation of the extract from Ginkgo biloba leaves which is substantially free of alkylphenol compounds and which has a high content of flavone glycosides, ginkgolides and bilobalide. The method of the present invention should, in contrast to the known methods in DE-B 17 67 098 and DE-B 21 17 429, succeed in removing the alkylphenol compounds without the use of chlorinated aliphatic hydrocarbons. The use of chlorinated hydrocarbons in technical processes is very problematic because of the occupational medical risks, the potential danger of these compounds to the environment and the possibility of undesirable residues in pharmaceuticals.

Finally, it is the object of the invention to provide pharmaceuticals which contain this Ginkgo biloba extract with a high content of flavone glycosides, ginkgolides and bilobalide and where there is substantially no danger of allergic reactions, precisely because of the removal of the alkylphenol compounds.

The invention therefore relates to an extract from Ginkgo biloba leaves which is substantially free of alkylphenol compounds, which has a high flavone glycoside content and which contains most of the ginkgolides and the bilobalide originally present in the leaves. Preferably the extract in the present invention should contain

- 20 to 30 weight percent, in particular 22 to 26 weight percent, flavone glycosides,
- 2.5 to 4.5 weight percent of ginkgolides A, B, C and J (in total),
- 2.0 to 4.0 weight percent bilobalide,
- less than 10 ppm, in particular less than 1 ppm, alkylphenol compounds and
- less than 10 weight percent proanthocyanidins.

In addition, the invention relates to a method of preparation of this Ginkgo biloba extract from Ginkgo biloba leaves.

More specifically, a method is described for the preparation of an extract from the leaves of Ginkgo biloba which is substantially free of alkylphenol compounds and has a high flavone glycoside content and a content of ginkgolides and bilobalide which corresponds to most of these components originally present in the leaves. The method comprises an extraction of the leaves with aqueous acetone, and aqueous alkanol of 1 to 3 C-atoms or anhydrous methanol. The lipophilic components are removed by at least one treatment with ammonium sulfate and a subsequent extraction with methylethylketone or a mixture of methylethylketone and acetone, as well as a treatment with a lead compound or an insoluble polyamide. The method is characterized in that most of the organic solvent is separated from the extract from the leaves containing the aqueous organic solvent, and the remaining aqueous solution is diluted to a solids content of 5 to 25 weight percent, preferably approximately 15 to 20 weight percent, and left to cool and stand until a precipitate forms from the lipophilic components which do not dissolve well in water. This precipitate is then separated, and the aqueous alcohol solution obtained following the treatment with the lead compound is extracted with an aliphatic or cycloaliphatic solvent with a boiling point of approximately 60°–100° C. in order to further separate the alkylphenol compounds.

Furthermore, a method is described for the preparation of an extract from Ginkgo biloba leaves, containing: 20 to 30 weight percent, preferably 22 to 26 weight percent, flavone glycosides; 2.5 to 4.5 weight percent ginkgolides A, B, C and J (in total); 2.0 to 4.0 weight percent bilobalide; less than 10 ppm, preferably less than 1 ppm, alkylphenol compounds; and less than 10 weight percent proanthyocyanidins. This method is characterized in that the fresh or dried green leaves of Ginkgo biloba are extracted at a temperature of approximately 40° to 100° C. with aqueous acetone, an aqueous alkanol of 1 to 3 C-atoms, or anhydrous methanol. Most of the organic solvent is then separated from the extract to a maximum content of 10 weight percent, preferably a maximum of 5 weight percent, whereby water can be added in the last steps of distillation. The remaining concentrated aqueous solution is diluted with water to a solids content of 5 to 25 weight percent, preferably 15 to 20 weight percent, and left to cool, while being stirred, to a temperature below 25° C., preferably approximately 10° to 12° C. The solution is left to stand until a precipitate forms and the resultant precipitate, consisting of the lipophilic components which do not dissolve well in water, is removed. The extract obtained is concentrated to a solids content of 50 to 70%, and the concentrate obtained is diluted with water and ethanol so that a solution is obtained which contains 50 weight percent of water and 50 weight percent of ethanol with a solids content of 10 weight percent. An aqueous solution of a lead salt such as lead acetate, lead hydroxide acetate or lead nitrate, or an aqueous suspension of lead hydroxide, preferably a solution of lead hydroxide acetate, is added to the thus obtained solution until a change in color from brown to umber takes place, and the precipitate formed is removed. The remaining aqueous-alcohol solution is extracted with an aliphatic or cycloaliphatic solvent with a boiling point of approximately 60° to 100° in order to further remove the alkylphenol compounds. The remaining aqueous-alcohol solution is concentrated under reduced pressure to a minimum ethanol content of approximately 5% and ammonium sulfate is added up to a content of 20 weight percent. The solution obtained is extracted with a mixture of methylethylketone and ethanol in a ratio of 9:1 to 4:6, preferably 4:6. The resultant organic phase is concentrated to a solids content of 50 to 70 weight percent. Finally, the resultant concentrate is dried under reduced pressure at a maximum temperature of 60° to 80° C. to a dry extract with a water content of less than 5%. Or, instead of a lead salt, a polyamide such as polyamide-6, polyamide-6,6 or cross-linked polyvinyl pyrrolidone (Polyvidon) can also be used. In contrast to the method of separating the lipophilic components described in DE-B 17 67 098, the aqueous alcohol or aqueous acetone crude extract is not directly subjected to liquid-liquid-extraction with a chlorinated aliphatic hydrocarbon, but rather most of the lipophilic components, which precipitate on distillation of the organic solvent components and dilution with water to a maximum content of 10 weight percent, preferably 5 weight percent, are separated by filtration. The alkylphenol compounds, the chlorophyll, the fatty acid derivatives and the biflavones precipitate due to their lower solubility in water and can be separated by filtration. Under these conditions, the desired components of the Ginkgo biloba extract remain dissolved. The alkylphenol compounds are reduced further to a content of less than 10 ppm in a subsequent degreasing step.

The extract obtained by extraction of the aqueous solution with methylethylketone/acetone, according to Example 5 in DE-B 17 67 098, is freed from the solvent by distillation. The residue is dissolved in 20 to 60 percent of aqueous ethanol until it has a solids content of 5 to 20%, preferably approximately 10%, and to this solution is added an aqueous solution of a lead salt, as in Example 1 and 2 in DE-B 21 17 429. After separation of the lead precipitates, the aqueous ethanol solutions obtained can be subjected either directly or after dilution with water to a ethanol content of preferably 30%, to a multistage liquid-liquid-extraction with an aliphatic or cycloaliphatic hydrocarbon (boiling point of approximately 60° to 100° C.). The filtrate obtained according to Example 3 (DE-B 21 17 429) can likewise be used either directly or after adjusting the ethanol content to approx. 30%.

In pharmacological experimental models, the extract prepared according to the present invention has radical scavenging properties and properties which stimulate the circulation of blood, prevent ischemic disorders and inhibit platelet aggregations.

In addition, the invention relates to pharmaceuticals which are characterized by a content of Ginkgo biloba extract.

The Ginkgo biloba extract of the invention can be processed in the usual way for the preparation of pharmaceuticals e.g. to solutions, coated tablets, tablets or injection preparations. The pharmaceuticals in the invention are used for the treatment of peripheral and cerebral arterial circulatory disturbances. The examples illustrate the invention. Parts and percentage data refer to weight unless otherwise stated.

EXAMPLE 1

100 kg of dry Ginkgo biloba leaves are crushed in a mill to a particle size of less than 4 mm. After adding 750 kg of 60 weight percent aqueous acetone the mixture is stirred intensively for 30 minutes at a temperature of 57° to 59° C. The solid residue is separated by filtration or centrifugation and subjected to a second extraction under the same conditions. The extracts from the first and second extraction steps are combined. The ginkgolic acid content (based on the dry extract) equals approximately 13,000 ppm. The extract is concentrated under reduced pressure to a solids content of 30 to 40% and a maximum of approximately 5 weight percent acetone. By adding water, the concentrate is diluted to double volume and, while being stirred, left to cool to approximately 12° C. A precipitate forms which contains most of the ginkgolic acids, that is, the alkylphenol compounds, present in the leaves. After one hour at this temperature, the resultant precipitate is separated by centrifugation and discarded.

The ginkgolic acid content in the resultant aqueous supernatant (based on the dry extract) equals approximately 320 ppm.

30 parts of ammonium sulfate are added to 100 parts of the aqueous solution. The mixture is stirred. After the ammonium sulfate has dissolved, a liquid-liquid-extraction is carried out twice with a mixture of methylethylketone and acetone in a ratio of 6:4 to 1:1, whereby the organic solvent added is the equivalent of half the volume of the aqueous solution and, after intensive stirring and pumping, the organic upper phase formed on completion of the mixing process is removed.

The methylethylketone acetone solution is then concentrated under reduced pressure to a solids content of 50 to 70%. This concentrate is diluted with water and 95 weight percent ethanol so that a solution with 10 weight percent dry extract in 50 weight percent aqueous ethanol is obtained. While stirring intensively, an aqueous solution of lead hydroxide acetate is added in small quantities to this solution until there is a change in colour from brown to umber (brown with a green cast). The lead-tannin precipitate which forms is separated by centrifugation.

The supernatant from the lead-tannin precipitation is subjected to a liquid-liquid-extraction with n-hexane in order to further remove the alkylphenol compounds. In this step, the alcohol-aqueous filtrate is stirred at least three times at room temperature, each time with ⅓ of its volume of n-hexane.

The aqueous-alcohol extract solution is then concentrated under reduced pressure to an ethanol content of less than approximately 5%. 20 parts of ammonium sulfate are dissolved in 100 parts of this solution and then a liquid-liquid-extraction is carried out with a mixture of methylethylketone and ethanol in a volumetric ratio of 6:4, whereby extraction with the organic solvent mixture is carried out twice, each time with the equivalent of half the volume of the aqueous solution. The organic phase is separated and stirred with 20% of its weight of ammonium sulfate. A possible phase of water and the undissolved ammonium sulfate are removed.

The clear extract solution is concentrated to a solids content of 50 to 70 weight percent. This concentrate is dried under reduced pressure at a maximum product temperature of approximately 60° to 80° C. to a dry extract with a water content of less than 5%.

From 100 kg of Ginkgo leaves, 2.5 kg of Ginkgo biloba extract with a content of approximately 24 weight percent flavone glycosides, approximately 3.6 weight percent ginkgolides, approximately 2.9 weight percent bilobalide, approximately 6.5 weight percent proanthocyanidins and less than 1 ppm alkylphenol compounds are obtained.

EXAMPLE 2

Solution for oral administration:
100 ml solution contains:

| | |
|---|---|
| Ginkgo biloba extract | 4.0 g |
| ethanol | 50.0 g |
| demineralised water to | 100.0 ml |

EXAMPLE 3

Coated tablets:
1 tablet contains:

| | | |
|---|---|---|
| Ginkgo biloba extract | | 40.00 mg |
| microcrystalline cellulose | | 100.00 mg |
| lactose | | 80.00 mg |
| colloidal silicic acid | | 25.00 mg |
| talcum (in core) | | 4.50 mg |
| magnesium stearate | | 0.50 mg |
| hydroxypropyl methylcellulose | | 12.00 mg |
| ferric oxide pigment | | 0.10 mg |
| talcum (in coat) | | 0.50 mg |
| weight of a coated tablet | approx. | 262.60 mg |

I claim:

1. An extract comprising 20 to 30 weight percent flavone glycosides, 2.5 to 4.5 weight percent of ginkogolides A, B, C and J, 2.0 to 4.0 weight percent bilobalide, less than 10 ppm alkylphenol compounds and less than 10 weight percent proanthocyanidins.

2. The extract of claim 1 containing about 22 to 26% by weight flavone glycosides.

3. The extract of claim 1 containing less than 1 ppm alkylphenol compounds.

4. A pharmaceutical composition useful for the treatment of peripheral and cerebral arterial circulatory disorders comprising a Ginkgo biloba extract of claim 1 in a pharmaceutical carrier wherein the extract concentration is sufficient to alleviate the circulatory disorders.

5. A method of preparing an extract from the leaves of Ginkgo biloba which is substantially free of alkylphenol compounds and having a high content of flavone glycosides and comprising substantially all of the ginkgolides and bilobalide originally present in the leaves, the method comprising the steps of a) extracting the leaves with an organic solvent selected from the group consisting of aqueous acetone, an aqueous alkanol having one to three carbon atoms and anhydrous methanol;

b) separating most of the organic solvent from the extract of step (a) to form an aqueous solution;

c) diluting the aqueous solution with water to a solids content of 5 to 25 weight percent;

d) cooling the diluted aqueous solution to precipitate and separate lipophilic components from the diluted aqueous solution;

e) treating the aqueous solution from step (d) with ammonium sulfate and and then extracting the aqueous solution with methylethylketone, acetone, or a mixture of methylethylketone and acetone;

f) diluting the extract from step (e) with water and alcohol to form an aqueous alcohol solution;

g) treating the aqueous alcohol solution with a lead compound or an insoluble polyamide;

h) extracting the treated aqueous alcohol solution with an aliphatic or cycloaliphatic solvent having a boiling point of about 60°–100° C. to further remove the alkylphenol compounds; and i) recovering a dry extract.

6. The method of claim 5 wherein the solids content of step (c) is about 15 to 20% by weight.

7. A method of preparing an extract from Ginkgo biloba leaves, containing 20 to 30 weight percent flavone glycosides, 2.5 to 4.5 weight percent of ginkgolides selected from ginkgolide A, B, C and J or mixtures thereof, 2.0 to 4.0 weight percent bilobalide, less than 10 ppm alkylphenol compounds and less than 10 weight percent proanthocyanidins comprising the steps of:

(a) extracting fresh or dried green leaves of Ginkgo biloba at a temperature of approximately 40° to 100° C. with an organic solvent selected from the group consisting of aqueous acetone, an aqueous alkanol of 1 to 3 C-atoms and anhydrous methanol, (b) distilling the extract from step (a) to remove the organic solvent to a maximum content of 10 weight percent to form a concentrated aqueous solution, (c) diluting the concentrated aqueous solution with water to a solids content of 5 to 25 weight percent and then cooling the diluted aqueous solution to a temperature below 25° C. to precipitate and separate the lipophilic components from the diluted aqueous solution, (d) adding ammonium sulfate to the aqueous solution from step (c) to a concentration of 30 weight percent and extracting said solution with methylethylketone or a mixture containing methylethylketone and acetone in a ratio from about 9:1 to 4:6, (e) concentrating the extract from step (d) to a solids content of 50 to 70% and then diluting with water and ethanol to form an aqueous alcohol solution containing about 50 weight percent of water and about 50 weight percent of ethanol with a solids content of about 10 weight percent, (f) adding an aqueous solution of a lead salt or an aqueous suspension of lead hydroxide to the aqueous alcohol solution of step (e) until a change in color from brown to umber takes place and precipitate is formed and separated, (g) extracting the aqueous alcohol solution from step (f) with an aliphatic or cycloaliphatic solvent having a boiling point of about 60° to 100° C. to further remove alkylphenol compounds, (h) concentrating the aqueous alcohol solution from step (g) under reduced pressure to a maximum ethanol content of about 5% and then adding ammonium sulfate up to about 20 weight percent, (i) extracting the aqueous alcohol solution from step (h) with a mixture of methylethylketone and ethanol in a ratio from about 8:2 to 5:5 to form an organic phase extract, (j) concentrating the organic phase extract to a solids content of 50 to 70 weight percent, and (k) drying the resultant concentrate from step (j) under reduced pressure at a maximum temperature of 60° to 80° C. to form a dry extract with a water content of less than 5%.

8. The method of claim 7 wherein the prepared extract contains about 22 to 26% by weight flavone glycosides.

9. The method of claim 7 wherein the prepared extract contains less than 1 ppm alkylphenol compounds.

10. The method of claim 7 wherein the extract of step (b) contains a maximum of 5 weight percent organic solvent.

11. The method of claim 7 wherein the solids content of step (c) is about 15 to 20% by weight.

12. The method of claim 7 wherein the extract of step (c) is cooled to about 10° to 12° C.

13. The method of claim 7 wherein the methylethylketone and acetone mixture of step (d), step (i), or step (d) and step (i) is in a ratio of 6 to 4.

14. The method of claim 7 wherein the lead salt in step (f) is selected from the group consisting of lead acetate, lead hydroxide acetate and lead nitrate.

15. The method of claim 7 wherein lead hydroxide acetate is added to the aqueous solution of step (f).

16. A pharmaceutical composition comprising a Ginkgo biloba extract prepared according to the process of claim 5, 6, 7, 8, 9, 10, 11, 12, 13, or 14 in a pharmaceutical carrier wherein the extract concentration is sufficient to alleviate circulatory disorders.

* * * * *